United States Patent
Sacrini et al.

[11] 3,956,319
[45] May 11, 1976

[54] ORGANIC PEROXIDES DERIVED FROM UNSATURATED COMPOUNDS

[75] Inventors: Egeo Sacrini; Claudio Cavallotti, both of Milan, Italy

[73] Assignee: The B. F. Goodrich Company, Akron, Ohio

[22] Filed: Mar. 3, 1975

[21] Appl. No.: 554,473

Related U.S. Application Data

[62] Division of Ser. No. 53,267, July 8, 1970, Pat. No. 3,896,176.

[30] Foreign Application Priority Data

July 29, 1969 Italy .................................. 20222/69

[52] U.S. Cl. ..................... 260/346.1 R; 260/610 R
[51] Int. Cl.² ............... C07C 307/00; C07C 179/00
[58] Field of Search .......... 260/610 R, 347.8, 346.1; 532/67

[56] References Cited
UNITED STATES PATENTS

| | | | |
|---|---|---|---|
| 3,296,184 | 1/1967 | Portolani et al. | 260/610 R |
| 3,822,317 | 7/1974 | D'Angelo et al. | 260/610 |

*Primary Examiner*—James O. Thomas, Jr.
*Assistant Examiner*—W. B. Lone
*Attorney, Agent, or Firm*—Hubbell, Cohen, Stiefel & Gross

[57] ABSTRACT

New organic peroxides having the formula

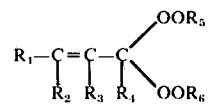

may be prepared by reacting a monohydroperoxide selected from $R_5OOH$ and $R_6OOH$ with an unsaturated carbonyl compound having the formula

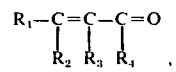

the reaction being carried out in the presence of an acid catalyst at a temperature between about −30°C and +80°C, the molar ratio of the carbonyl compound to the hydroperoxide being between about 1:2 and 1:10. The new organic peroxides are particularly useful for crosslinking plastomers, vulcanizing elastomers, and as initiators for radical polymerizations.

9 Claims, No Drawings

ORGANIC PEROXIDES DERIVED FROM UNSATURATED COMPOUNDS

This is a division, of application Ser. No. 53,267, filed July 8, 1970, now U.S. Pat. No. 3,896,176.

BACKGROUND OF THE INVENTION

1. Field of the Invention

The present invention relates to new organic peroxides and more particularly to new organic peroxides which have a double peroxidic function and are derived from unsaturated compounds, as well as to the use of these new organic peroxides in the crosslinking of plastomers, in the volcanization of elastomers and as organic reactants.

2. Description of the Prior Art

Organic peroxides are used as initiators for radical polymerization, vulcanizing agents for elastomers, and cross-linking agents for thermoplastic polymers. A discussion of typical organic peroxides used in the prior art, their preparation, and some difficulties associated with the preparation and use of some prior art peroxides appears in U.S. Pat. No. 3,489,730, which was issued Jan. 13, 1970, to the assignee hereof and the contents of which are hereby incorporated herein by reference.

The present invention provides a class of new organic peroxides having good stability and low volatility, which peroxides are particularly suited and interesting both as cross-linking agents for plastomers and as vulcanizing agents for elastomers.

SUMMARY OF THE INVENTION

The present invention provides a new series of peroxides with a double peroxidic function characterized by one or more unsaturated bonds and having the general formula:

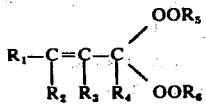

wherein $R_1$ is selected from the group consisting of unsubstituted, alkyl substituted and halogen substituted cycloalkyl radicals having 5–30 C; unsubstituted, alkyl substituted, hydroxy substituted and halogen substituted phenyl radicals having 6–26 C; and unsubstituted, alkyl substituted and halogen substituted heterocyclic radicals having 4–15 C; $R_2$ is selected from the group consisting of hydrogen, alkyl radicals having 1–12 C, unsubstituted, alkyl substituted and halogen substituted cycloalkyl radicals having 5–°C halogen substituted alkyl radicals having 1–12 C; and unsubstituted, alkyl substituted and halogen substituted phenyl radicals; and $R_1$ and $R_2$ together with the carbon atom to which they are bonded may form a cycloaliphatic ring selected from the group consisting of unsubstituted and alkyl, phenyl, phenylalkyl, alkylidene and phenylalkylidene substituted cycloaliphatic rings having 5–30 C; $R_3$ and $R_4$ are each selected from the group consisting of hydrogen, alkyl radicals having 1–12 C, unsubstituted, alkyl substituted and halogen substituted cycloalkyl radicals having 5–20 C; unsubstituted, alkly substituted and halogen substituted phenyl radicals having 6–20 C; halogen substituted alkyl radicals having 1–12 C, and halogen substituted phenylalkyl radicals having 7–20 C; and $R_3$ and $R_4$ taken together with the two adjacent carbon atoms to which they are respectively bonded may form a cycloaliphatic ring selected from the group consisting of unsubstituted and alkyl, phenyl, phenylalkyl, alkylidene, phenylalkylidene and hydroxy phenylalkylidene substituted cycloaliphatic rings having 5–25 C; $R_5$ and $R_6$ are each selected from the group consisting of alkyl radicals having 4–12 C, phenylalkyl radicals having 9–18 C, unsubstituted, alkyl substituted and halogen substituted cycloalkyl radicals having 5–21 C; unsubstituted, alkyl substituted and halogen substituted phenylcycloalkyl radicals having 9–25 C; halogen substituted alkyl radicals having 4–12 C, and halogen substituted phenylalkyl radicals having 9–18 C.

DESCRIPTION OF THE PREFERRED EMBODIMENTS

Tertiary alkyl groups, for example, ter.-butyl, ter.-amyl and cumyl, are preferred as the $R_5$ and $R_6$ radicals.

Examples of compounds of the present invention, within the above general formula, include:

a. 1-phenyl-3,3-di(ter.-butyl-peroxy)-propene-1;
b. 1-phenyl-3,3-di(cumyl-peroxy)-propene-1;
c. 1-phenyl-3,3-di(ter.butyl-peroxy)-butene-1;
d. 1-phenyl-3,3-di(cumyl-peroxy)-butene-1;
e. 1-phenyl-3-ter.-butyl-peroxy-3-cumyl-peroxy-butene-1;
f. 1-cyclohexylidene-2,2-di(ter.-butyl-peroxy)-ethane;
g. 1-furyl-3,3-di(ter.-butyl-peroxy)-propene-1
h. 1-furyl-2-methyl-3,3-di(ter.-butyl-peroxy)-propene-1;
i. 1,1-di(ter.-butyl-peroxy)-2-benzylidene-cyclohexane;
l. 1,1-di(ter.-butyl-peroxy)-2,6-di(4-hydroxy-benzylidene)cyclohexane; and
m. 1,1-di(ter.-butyl-peroxy)-2,6-di(4-isopropyl-benzylidene)cyclohexane;
n. 1-cyclohexyl-3,3-di(ter-butyl-peroxy)-butene-1;
o. 2,3-di(phenyl)-4-di(ter-butyl-peroxy)-butene-2;
p. 1-phenyl-3,3-di(cyclohexen-2-yl-1-peroxy)propene-1;
q. 1-phenyl-3,3-di(cyclohexen-2-yl-1-ethyl-peroxy)-propene-1;
r. 1-phenyl-3,3-di(tetralin-1-peroxy)propene-1;
s. 1-phenyl-3,3-di(tetralin-1-methyl-1-peroxy)propene-1.

The diperoxides of this invention have the unusual properties of having good stability and low volatility at temperatures higher than room temperature. These properties permit the compounds to be incorporated in plastomers as crosslinking agents and in saturated elastomers as vulcanizing agents without giving rise to the troublesome secondary phenomena (for instance pre-vulcanization and pre-crosslinking) which arise when using less stable, more volatile, prior art peroxides.

In accordance with a preferred embodiment, the diperoxides of the invention may be prepared by reacting an unsaturated carbonyl derivative, dissolved in a suitable solvent, with an organic hydroperoxide in the presence of an acid catalyst at a temperature between about −30° and +80°C, preferably between about −10° and +50°C.

The unsaturated carbonyl compounds which may be used in the foregoing reaction have the general formula

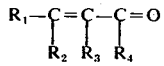

wherein $R_1$, $R_2$, $R_3$ and $R_4$ are as defined above. Examples of such carbonyl compounds include, for instance, cinnamic aldehyde, furyl-acrylic aldehyde, alpha-cyclo-hexyhidene-acetaldehyde, alphabenzylidene-acetone and 2,6-benzylidene-cyclohexanone.

The hydroperoxides which may be used in the reaction have the general formula R-OOH wherein R represents $R_5$ and $R_6$ as defined above. Examples of such compounds include: ter.-butyl hydroperoxide, and substituted derivatives thereof; cumyl-hydroperoxide and substituted derivatives thereof; 1,3 diisopropylbenzene-α-monohydroperoxide and 1,4 diiso-propylbenzene-α-monohydroperoxide; 1-methyl-cyclohexyl-hydroperoxide; 2-methyl-2-hydroperoxy-butyn-3; 1-menthane-hydroperoxide; and 1-phenyl-cyclohexyl hydroperoxide.

The solvents which may be employed in the reaction include for example, linear aliphatic hydrocarbons having 6 to 10 C, linear aliphatic halogenated hydrocarbons, having 1 or 2 c and from 1 to 4 cl aromatic hydrocarbons, having from 6 to 9 C, which may be halogenated with 1 or 2 Cl, cycloaliphatic hydrocarbons having 6 to 10 C, and ethers, for instance ethylether.

The molar ratio of unsaturated carbonyl compound to hydroperoxide is between about 1:2 and 1:10, preferably between about 1:2.5 and 1:5.

The catalysts used are preferably sulfonic acids, such as for instance, para-toluene sulphonic acid.

The new diperoxides of the present invention are soluble in chlorinated and unchlorinated aliphatic and aromatic hydrocarbon solvents, and in aliphatic esters. A particular feature of this invention is that the diperoxides of this invention are excellent crosslinking agents for plastomers, vulcanizing agents for elastomers and initiators for radical polymerization. The use of the diperoxides defined above for the crosslinking of plastomers is particularly applicable to the polyolefins and more particularly to polyethylene.

The crosslinking of polyethylene with the peroxides of the present invention results in a product having improved mechanical properties at high temperatures, reduced fragility at low temperatures and reduced solubility in aliphatic and aromatic hydrocarbons, even chlorinated ones. Furthermore, the crosslinked polyethylene has increased resistance to light, weather and to ageing.

The crosslinking is carried out in accordance with this aspect of the present invention at a temperature between about 100° and 200°C, preferably between about 145° and 165°C, at a pressure between about 50 and 200 kg/cm² and for periods of from about 5 to 60 minutes, preferably from about 10 to 30 minutes. The concentration of the peroxide is between about 0.5 and 10% by weight, preferably between about 2 and 5% by weight, based on the weight of the plastomer.

The vulcanization of elastomers, for example, ethylene/propylene copolymers, in accordance with the present invention may be carried out at a temperature between about 140° and 190°C. preferably between about 150° and 170°C, for periods of from about 5 to 200 minutes, preferably between about 5 to 15 minutes. The concentration of the peroxide is between about 0.5 and 10% by weight, preferably between about 2 and 5% by weight, based on the weight of the elastomer.

Particularly suitable vulcanization mixes for vulcanizing ethylene/propylene copolymer have compositions within the following ranges:

| | |
|---|---|
| ethylene/propylene copolymer | 100 parts by weight |
| carbon black | 20 to 80 parts by weight |
| ZnO | 1 to 10 parts by weight |
| sulfur | 0.15 to 0.5 parts by weight |
| peroxide | 0.005 to 0.02 moles. |

The most notable advantages afforded by the use of the diperoxides of the present invention in the crosslinking of plastomers and in the vulcanization of saturated elastomers include: practically odorless crosslinked and vulcanized products; absence of "blooming" phenomena; short vulcanization times and low vulcanization temperatures; the greater effectiveness of the new diperoxides remains unaltered even in the presence of known fillers, reinforcing agents (for instance carbon black, Mg hydrosilicate), additives of the type ageing resistant plastified and homogenized masses can be obtained without pre-crosslinking or pre-vulcanization phenomena which hinder the further processing.

The possibility of obtaining plastified and homogenized masses without pre-crosslinking or pre-vulcanization phenomena is due to the fact that the peroxides do not thermally decompose to the mixing temperature giving rise to the beginning of the pre-crosslinking and pre-vulcanization phenomena.

The following examples are presented to further illustrate the present invention.

EXAMPLE 1

200 g of anhydrous benzene and 131.5 g of 80% ter-butyl hydroperoxide were introduced into a flask at ambient temperature provided with a stirrer. The temperature was then increased to 40°C and, during 10 minutes, there were simultaneously added 51.6 g of 98% cinnamic aldehyde and 100 g of a benzene/methanol solution of paratoluensulfonic acid, having the following composition by weight:

0.14% of paratoluenesulfonic acid, 1.42% of anhydrous methanol, and 98.44% of anhydrous benzene.

The mixture was then stirred for 3 hours at 40°C. Thereafter, the organic solution was washed with 8% aqueous solution of $NaHCO_3$, then with 5% aqueous NaOH, and finally with water to a pH of 6.5.

The solvent was then removed under vacuum (final pressure, 0.2 mm Hg) at 30°C, obtaining 92 g of a white crystalline product as residue.

After repeated recrystallizations from methanol, there were obtained 75 g of a solid crystalline product which was identified as 1-phenyl-3,3-di(ter.-butylperoxy)-propene-1. This product had product had the following characteristics:

| | |
|---|---|
| Melting point: | 58–59°C |
| iodometric titer: | 98% |
| decomposition temperature: | 118°C |
| half life at 120°C: | 30 minutes |
| carbon content, weight % found: | 69.0 |
| carbon content, weight % calculated: | 69.36 |
| hydrogen content, weight % found: | 9.1 |
| hydrogen content, weight % calculated: | 8.90. |

EXAMPLE 2

200 g of normal hexane and 120 g of 90% ter.-butyl hydroperoxide were introduced into a flask of ambient temperature provided with a stirrer. The temperature was increased to 42° to 45°C and, during 10 minutes, there were simultaneously introduced 48.8 g of distilled furyl-acrylic aldehyde and 160 g of a benzene/methanol solution of paratoluenesulfonic acid having the following composition by weight:

1.42% of anhydrous methanol, 98.44% of anhydrous benzene and 0.14% of paratoluenesulfonic acid, i.e., the same composition as the solution employed in Example 1.

This mixture was then stirred for 3 hours and 30 minutes at a temperature of 42° to 45°C. The organic solution was then washed with water, with an 8% NaHCO$_3$ solution and then again with water to a pH of 6.5. The solvent was removed under vacuum at 40°C, with a final pressure of 0.2 mmHg.

The solid residue (119 g) was crystallized from methanol and there were thus obtained 101 g of a light yellow crystalline product which was identified as 1-furyl-3,3-di(ter.-butyl-peroxy)-propene-1.

The product had the following characteristics:

| | |
|---|---|
| melting point: | 56–57°C |
| iodometric titer: | 99.5% |
| decomposition temperature: | 101°C |
| half life at 118°C: | 30 minutes |
| carbon content, weight % found: | 64.0% |
| carbon content, weight % calculated: | 63.36% |
| hydrogen content, weight % found: | 8.7% |
| hydrogen content, weight % calculated: | 8.51%. | then distilled under vacuum at 30° to 32°C, thereby obtaining 14 g of an oily yellow product identified as 1-phenyl-3,3-di(cumyl-peroxy)-propene-1. This product showed the following characteristics:

| | |
|---|---|
| iodometric titration: | 77.6% |
| $n_D^{20}$: | 1.5586 |
| decomposition temperature: | 125°C |
| half life at 119°C: | 30 minutes |
| carbon content, weight % found: | 77.0% |
| carbon content, weight % calculated: | 77.4% |
| hydrogen content, weight % found: | 7.3% |
| hydrogen content, weight % calculated: | 7.22% |

EXAMPLE 4

Vulcanization:

The vulcanization tests were carried out on mixes of an ethylene/propylene copolymer, having a molar ratio ethylene/propylene 50/50 and a viscosity Mooney ML(1+4) 100°C = 35. In Table 1 there are compared the vulcanization rates determined on equivalent mixes containing as peroxides, respectively, 1-phenyl-3,3-di(ter.-butyl-peroxy)-propene-1; 1-furyl-3,3-di(ter.-butyl-peroxy)-propene-1 and dicumyl peroxide.

The vulcanization rate was determined at 177°C on a Monsanto TM-10 rheometer. The mixes used had the following composition:

| | |
|---|---|
| ethylene/propylene copolymer | 100 parts by weight |
| carbon black | 50 parts by weight |
| ZnO | 3 parts by weight |
| sulfur | 0.32 parts by weight |
| perozide | 0.01 moles. |

TABLE 1

| Peroxide | Vulcanization rate Parts per 100 g of ethylene/propylene copolymer g | moles | Vulcanization temperature °C | Vulcanization time minutes |
|---|---|---|---|---|
| phenyl-CH=CH-CH(OOC(CH$_3$)$_3$)(OOC(CR$_3$)$_3$) | 2.94 | 0.01 | 177 | 6 |
| furyl-CH=CH-CH(OOC(CH$_3$)$_3$)(COC(CH$_3$)$_3$) | 2.84 | 0.01 | 177 | 5 |
| Dicumylperoxide | 2.70 | 0.01 | 177 | 14 |

EXAMPLE 3

50 cc of benzene and 14.5 g. of 83.8% cumene hydroperoxide were introduced into a flask at ambient temperature provided with a stirrer. The temperature of the solution was then increased to 42° to 45°C. Then, during 15 minutes, there were simultaneously added, dropwise, a mixture consisting of 5.1 g of 98.2%, cinnamic aldehyde and 20 g of a solution of paratoluenesulfonic acid having the following composition by weight: 0.2% of paratoluenesulfonic acid, 1.4% of absolute ethyl alcohol and 98.4% of benzene.

This mixture was then stirred for 3 hours at 45°C, and at the end of this time it was washed with water, then with a 5% NaHCO$_3$ solution, then with 5% NaOH, and finally with water until neutral pH. The solvent was Table 2 compares the physical properties of the vulcanized products obtained by the use of 1-phenyl-3,3-di(ter.-butyl-peroxy)-propene-1; and 1-furyl-3,3-di(-ter.-butyl-peroxy)-propene-1, at vulcanization times between 5 and 60 minutes, at a vulcanization temperature of 150°C, with those of the vulcanized products obtained using dicumyl peroxide at 165°C for 30 minutes (these being the optimal conditions for dicumyl peroxide).

From the results set forth in Table 2 it appears evident that the peroxides of the present invention permit the use of a low vulcanization temperature while affording high vulcanization rates and better physical characteristics of the vulcanized product than those obtained by using dicumylperoxide at higher temperature (165°C) for longer periods of time (30 minutes).

Table 2

| Peroxide | Parts per 100 parts of ethylene/propylene copolymer moles | Parts per 100 parts of ethylene/propylene copolymer g. | Vulcanization Temperature °C | Time minutes | Tensile strength kg/cm² | Elongation at break % | Modulus at 100% Elongation kg/cm² | Modulus at 200% Elongation kg/cm² | Modulus at 300% Elongation kg/cm² | RHD hardness |
|---|---|---|---|---|---|---|---|---|---|---|
| CH=CH—CH(OOC(CH₃)₃)(OOC(CH₃)₃)–C₆H₅ | 0.015 | 4.41 | 150 | 5 | 215 | 550 | 20 | 43 | 92 | 63 |
| | | | | 10 | 218 | 460 | 25 | 66 | 127 | 65 |
| | | | | 15 | 192 | 370 | 24 | 67 | 137 | 65 |
| | | | | 30 | 208 | 400 | 25 | 71 | 138 | 65 |
| | | | | 60 | 192 | 400 | 25 | 65 | 133 | 65–66 |
| furyl-CH=CH—CH(OOC(CH₃)₃)(OOC(CH₃)₃) | 0.010 | 3.41 | 150 | 5 | 134 | 350 | 26 | 60 | 106 | 66 |
| | | | | 10 | 145 | 390 | 27 | 60 | 104 | 66 |
| | | | | 15 | 149 | 400 | 25 | 57 | 102 | 66 |
| | | | | 30 | 125 | 320 | 25 | 59 | 106 | 66 |
| | | | | 60 | 136 | 360 | 25 | 62 | 109 | 65 |
| Dicumylperoxide | 0.010 | 2.70 | 165 | 30 | 180 | 410 | 21 | 58 | 119 | 68 |

EXAMPLE 5

Crosslinking:

The crosslinking tests were carried out on mixes of low-density (0.918) polyethylene and peroxide. Table 3 sets forth the physical properties of the polyethylene crosslinked by using, respectively, the diperoxides prepared in Example 1 (1-phenyl-3,3-di(ter.-butyl-peroxy)-propene-1), Example 2 (1-furyl-3,3-di(ter.-butyl-peroxy)-propene-1), and a known diperoxide (dicumylperoxide).

The results thus obtained show the excellent crosslinking activity of the diperoxides of the invention

TABLE 3

| Peroxide | Moles of peroxide in 100 g of polyethylene | Crosslinking Time minutes | Crosslinking Temperature °C | Yield point kg/cm² | Tensile strength kg/cm² | Elongation at break in % | Degree of swelling in xylol at 80°C for 21 hours |
|---|---|---|---|---|---|---|---|
| None | — | 20 | 145 | 57.8 | 73 | 150 | soluble |
| C₆H₅—CH=CH—CH(OOC(CH₃)₃)(OOC(CH₃)₃) | 0.01 | 20 | 145 | 52 | 150 | 240 | 10.4 |
| furyl-CH=CH—CH(OOC(CH₃)₃)(OOC(CH₃)₃) | 0.01 | 20 | 145 | 57 | 140 | 400 | 14 |
| Dicumylperoxide | 0.01 | 20 | 145 | 52.9 | 132 | 456 | 21.3 |

The determination of the degree of swelling was carried out on the crosslinked product. By the term "degree of swelling" is meant the volume of solvent absorbed by a given volume of crosslinked polyethylene. The test method consists of suspending a small basket containing a plate of about 0.2 g of crosslinked polyethylene in a test tube containing 100 cc of xylene stabilized with 0.1 g of phenolic antioxidant, i.e., 4,4-thiobis(3-methyl-6-ter.-butyl-phenol). The operation is carried out at 80°C for 21 hours. The degree of swelling is given by the following formula:

$$1.07 \cdot \frac{(a-b)-c}{c} + 1$$

wherein $a$ = weight of the test sample after 21 hours at 80°C in xylene, $b$ = weight of test sample before the test, $c$ = weight of test sample after drying at the end of the test, $$1.07 = \frac{\text{density of polyethylene at 80°C}}{\text{density of xylene at 80°C}}$$

Variations can, of course, be made without departing from the spirit and scope of the invention.

Having thus described our invention, what we desire to secure by Letters Patent and hereby claim is:

1. An organic peroxide having the formula:

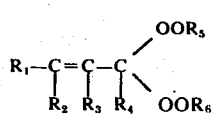

wherein $R_1$ is selected from the group consisting of furyl, alkyl substituted furyl radicals having 4–15 carbon atoms; $R_2$ is selected from the group consisting of hydrogen, alkyl radicals having 1–12 carbon atoms, cycloalkyl, alkyl substituted cycloalkyl radicals having 5–20 carbon atoms, alkyl radicals having 1–12 carbon atoms, and phenyl and alkyl substituted phhenyl radicals; $R_3$ and $R_4$ are each selected from the group consisting of hydrogen, alkyl radicals having 1–12 carbon atoms, cycloalkyl and, alkyl substituted cycloalkyl radicals having 5–20 carbon atoms; phenyl and alkyl substituted phenyl radicals having 6–20 carbon atoms; alkyl radicals having 1–12 carbon atoms, phenylalkyl radicals having 7–20 carbon atoms; and $R_3$ and $R_4$ taken together with the two adjacent carbon atoms to which they are respectively bonded may form a cycloaliphatic ring selected from the group consisting of alkyl, phenyl, phenylalkyl, alkylidene, phenylalkylidene and hydroxyphenylalkylidene substituted cycloaliphatic rings having 5–25 carbon atoms; $R_5$ and $R_6$ are each selected from the group consisting of alkyl radicals having 4–12 carbon atoms, phenylalkyl radicals having 9–18 carbon atoms; cyclalkyl and alkyl substituted cycloalkyl radicals having 5–21 carbon atoms; phenylcycloalkyl and alkyl substituted phenylcycloalkyl radicals having 9–25 carbon atoms; alkyl radicals having 4–12 carbon atoms and phenylalkyl radicals having 9–18 carbon atoms.

2. The peroxide of claim 1 wherein $R_5$ and $R_6$ are tertiary alkyl.

3. The peroxide of claim 2 wherein $R_5$ and $R_6$ are selected from the group consisting of tertiary butyl, tertiary amyl, and cumyl.

4. The peroxide of claim 1 which is selected from the group consisting of
 1-furyl-3,3-di(ter.-butyl-peroxy)-propene-1;
 1-furyl-2-methyl-3,3-di(ter.-butyl-peroxy)-propene-1.

5. A process for the preparation of an organic peroxide having the formula:

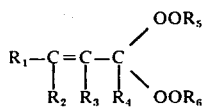

wherein $R_1$ is selected from the group consisting of furyl and, alkyl substituted furyl radicals having 4–15 carbon atoms; $R_2$ is selected from the group consisting of hydrogen, alkyl radicals having 1–12 carbon atoms, cycloalkyl and alkyl substituted cycloalkyl radicals having 5–20 carbon atoms, alkyl radicals having 1–12 carbon atoms; and phenyl and alkyl substituted phenyl radicals; $R_3$ and $R_4$ are each selected from the group consisting of hydrogen, alkyl radicals having 1–12 carbon atoms, cycloalkyl and alkyl substituted cycloalkyl radicals having 5–20 carbon atoms; phenyl and, alkyl substituted phenyl radicals having 6–20 carbon atoms; alkyl radicals having 1–12 carbon atoms, and phenylalkyl radicals having 7–20 carbon atoms; and $R_3$ and $R_4$ taken together with the two adjacent carbon atoms to which they are respectively bonded may form a cycloaliphatic ring selected from the group consisting of alkyl, phenyl, phenylalkyl, alkylidene, phenylalkylidene and hydroxyphenylalkylidene substituted cycloaliphatic rings having 5–25 carbon atoms; $R_5$ and $R_6$ are each selected from the group consisting of alkyl radicals having 4–12 carbon atoms, phenylalkyl radicals having 9–18 carbon atoms, cycloalkyl and alkyl substituted cycloalkyl radicals having 5–21 carbon atoms; phenylcycloalkyl and alkyl substituted phenylcycloalkyl radicals having 9–25 carbon atoms; alkyl radicals having 4–12 carbon atoms, and phenylalkyl radicals having 9–18 carbon atoms, this process comprising reacting a hydroperoxide selected from the group consisting of $R_5OOH$ and $R_6OOH$, wherein $R_5$ and $R_6$ are as defined above, with an unsaturated carbonyl compound, having the formula:

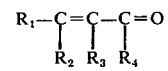

wherein $R_1$, $R_2$, $R_3$, $R_4$ are as defined above dissolved in a suitable solvent in the presence of a sulfonic acid catalyst at a temperature between about $-30°$ and $+80°C$., the molar ratio of said carbonyl compound to said hydroperoxide being between about 1:2 and 1:10.

6. The process of claim 5, wherein the said molar ratio is between about 1:2.5 and 1:5.

7. The process of claim 5, wherein said reaction temperature is between about $-10°$ and $50°C$.

8. The process of claim 5, wherein said sulfonic acid catalyst is p-toluene sulfonic acid.

9. The process of claim 5 which is carried out in a solvent selected from the group consists of linear aliphatic hydrocarbons having 6–10 carbon atoms, linear aliphatic halogenated hydrocarbons having 1 or 2 carbon atoms and from 1 to 4 chlorine atoms, aromatic hydrocarbons having from 6 to 9 carbon atoms which may be halogenated with 1 or 2 chlorine atoms, cycloaliphatic hydrocarbons having 6–10 carbon atoms and ethers.

* * * * *

UNITED STATES PATENT OFFICE
CERTIFICATE OF CORRECTION

Patent No. 3,956,319      Dated May 11, 1976

Inventor(s) EGEO SACRINI et al      Page 1 of 2

It is certified that error appears in the above-identified patent and that said Letters Patent are hereby corrected as shown below:

Column 1, line 28: "a class" should read -- a particular class --; line 54: "5-°C" should read -- 5-20 C. --.

Column 2, line 32: "g. 1-furyl-3,3-di(ter.-butyl-peroxy)-propene-1" should read -- g. 1-furyl-3,3-di(ter.-butyl-peroxy)-propene-1; --; line 38: "cyclohexane; and" should read -- cyclohexane; --.

Column 3, line 10: "cyclo-hexyhidene" should read -- cyclo-hexylidene --; line 26: "1 or 2 c and from 1 to 4 cl" should read -- 1 or 2 C and from 1 to 4 Cl --.

Column 4, line 61: "product had product had" should read -- product had --.

Column 5, line 29: "101°C" should read -- 104°C --.

Column 6, line 32: "perozide" should read -- peroxide --.

Columns 5-6, Table 1, in the heading: "ethyllene/propylene" should read -- ethylene/propylene; Table 1, first formula:

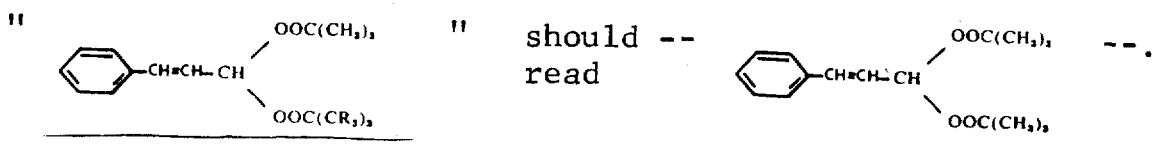

Signed and Sealed this

Tenth Day of August 1976

[SEAL]

Attest:

RUTH C. MASON
Attesting Officer

C. MARSHALL DANN
Commissioner of Patents and Trademarks

UNITED STATES PATENT OFFICE
CERTIFICATE OF CORRECTION

Patent No. 3,956,319  Dated May 11, 1976

Inventor(s) EGEO SACRINI et al  Page 2 of 2

It is certified that error appears in the above-identified patent and that said Letters Patent are hereby corrected as shown below:

Columns 5-6, Table 1, second formula:

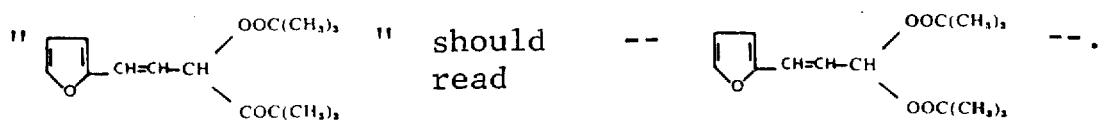

Column 8, line 7 of claim 1, after the formula: "phhenyl" shoudl read -- phenyl --.

Column 10, line 2 of claim 9: "consists" should read -- consisting --.

Signed and Sealed this

Tenth Day of August 1976

[SEAL]

Attest:

RUTH C. MASON
*Attesting Officer*

C. MARSHALL DANN
*Commissioner of Patents and Trademarks*